(12) United States Patent
Glacer et al.

(10) Patent No.: US 10,352,910 B2
(45) Date of Patent: Jul. 16, 2019

(54) GAS ANALYZER

(71) Applicant: Infineon Technologies AG, Neubiberg (DE)

(72) Inventors: Christoph Glacer, Munich (DE); Alfons Dehe, Reutlingen (DE); David Tumpold, Kirchheim (DE)

(73) Assignee: Infineon Technologies AG, Neubiberg (DE)

( * ) Notice: Subject to any disclaimer, the term of this patent is extended or adjusted under 35 U.S.C. 154(b) by 287 days.

(21) Appl. No.: 15/252,332

(22) Filed: Aug. 31, 2016

(65) Prior Publication Data

US 2018/0059066 A1   Mar. 1, 2018

(51) Int. Cl.
*G01N 33/00*    (2006.01)
*G01N 29/24*    (2006.01)
*G01N 29/14*    (2006.01)

(52) U.S. Cl.
CPC ......... *G01N 29/2418* (2013.01); *G01N 29/14* (2013.01); *G01N 29/2425* (2013.01); *G01N 33/004* (2013.01)

(58) Field of Classification Search
CPC ........... G01N 29/2425; G01N 29/2418; G01N 29/02; G01N 21/1702; G01N 2021/1704
See application file for complete search history.

(56) References Cited

U.S. PATENT DOCUMENTS

2003/0209669 A1*  11/2003  Chou ................. G01N 21/3504
                                                    250/343
2008/0277586 A1*  11/2008  Cardinale ............ G01M 3/002
                                                    250/339.13
2016/0282259 A1*   9/2016  Kolb .................... G01N 29/022

FOREIGN PATENT DOCUMENTS

DE      202015002315 U1 *  5/2015  ........... G01N 29/022
WO      WO-2017044435 A1 *  3/2017  ......... G01N 21/3504

* cited by examiner

*Primary Examiner* — Blake A Tankersley
(74) *Attorney, Agent, or Firm* — Viering, Jentschura & Partner MBB

(57) ABSTRACT

A gas analyzer is provided. The gas analyzer may include: a tubular housing having a housing wall extending along an axial direction of the tubular housing and surrounding a gas chamber configured to receive a gas to be analyzed therein, an excitation element positioned at a first axial end of the tubular housing and configured to selectively excite gas molecules of a specific type that is to be detected in the gas received in the gas chamber in a time-varying fashion, thereby generating acoustic waves, and a sensor positioned at a second axial end of the tubular housing and configured to detect acoustic waves generated by the excitation element.

23 Claims, 1 Drawing Sheet

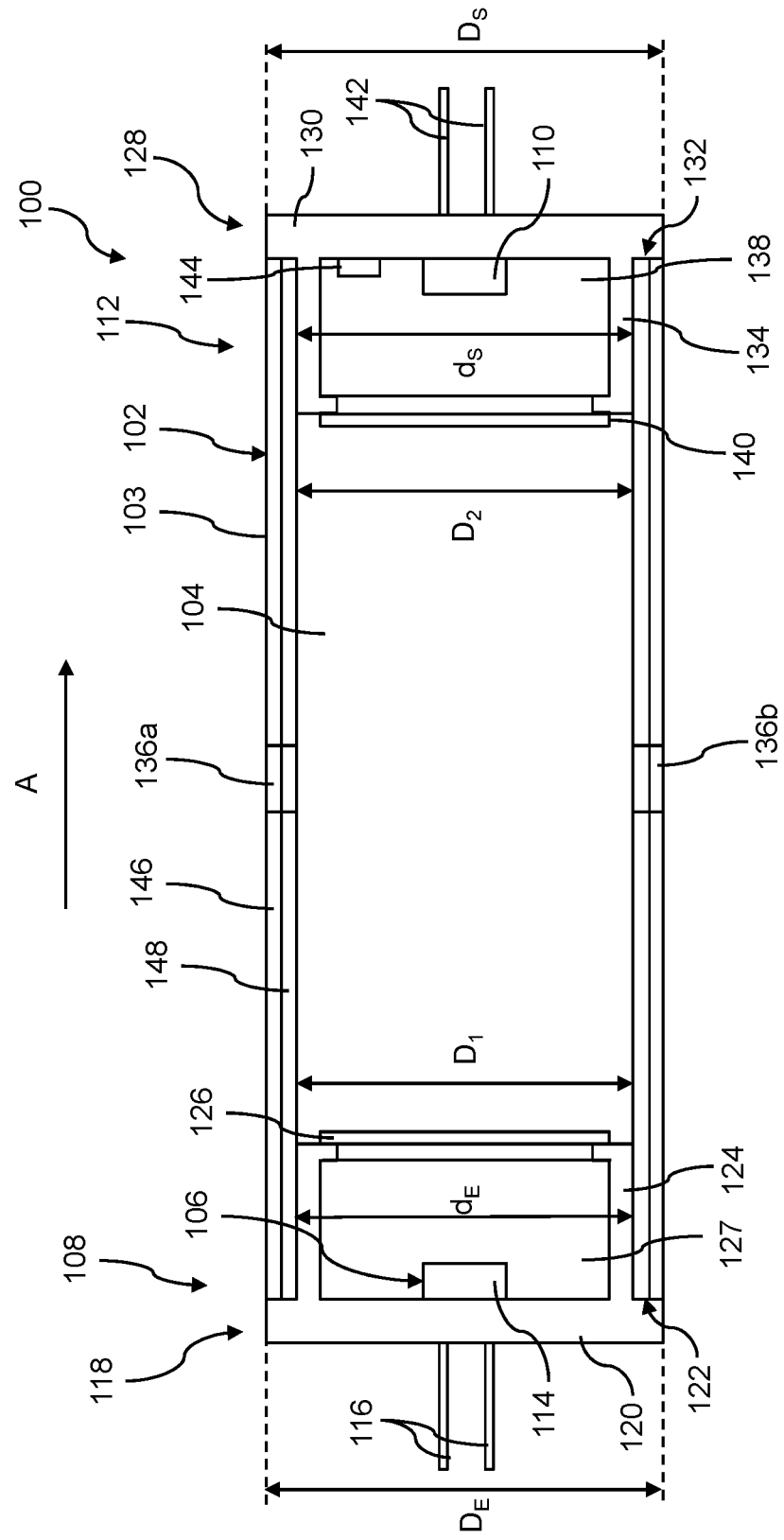

GAS ANALYZER

TECHNICAL FIELD

Various embodiments relate generally to a gas analyzer.

BACKGROUND

Gas analyzers, either configured as photoacoustic gas detectors or as non-dispersive spectrometers, provide a simple way of analyzing the composition of gases. Since the analysis of the composition of ambient air, e.g., due to pollution, is becoming increasingly important, it is desirable to provide a gas analyzer with a compact structure that is flexible at use.

SUMMARY

According to various embodiments, a gas analyzer is provided. The gas analyzer may include: a tubular housing having a housing wall extending along an axial direction of the tubular housing and surrounding a gas chamber configured to receive a gas to be analyzed therein, an excitation element positioned at a first axial end of the tubular housing and configured to selectively excite gas molecules of a specific type that is to be detected in the gas received in the gas chamber in a time-varying fashion, thereby generating acoustic waves, and a sensor positioned at a second axial end of the tubular housing and configured to detect acoustic waves generated by the excitation element.

According to various embodiments, a gas analyzer is provided. The gas analyzer may include: a tubular housing having a housing wall extending along an axial direction of the tubular housing and surrounding a gas chamber configured to receive a gas to be analyzed therein, a radiation source positioned at a first axial end of the tubular housing and configured to emit electromagnetic radiation that is configured to selectively excite gas molecules of a specific type that is to be detected in the gas received in the gas chamber, and a sensor positioned at a second axial end of the tubular housing and configured to detect electromagnetic radiation emitted by the radiation source.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 1 shows a schematic view of a gas analyzer.

DESCRIPTION

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

FIG. 1 shows a schematic view of a gas analyzer 100. The gas analyzer 100 may be configured as a photoacoustic gas analyzer including a tubular housing 102 having a housing wall 103 extending along an axial direction A of the tubular housing 102 and defining a gas chamber 104 configured to receive a gas to be analyzed therein. The photoacoustic gas analyzer 100 may further include an excitation element 106 positioned at a first axial end 108 of the tubular housing 102 and configured to selectively excite gas molecules of a specific type that is to be detected in the gas received in the gas chamber 104 in a time-varying fashion. The excitation element 106 may be configured to induce a specific atomic or molecular transition in gas molecules of the type that is to be detected and/or to excite various vibrational and/or rotational modes of said gas molecules. During the subsequent de-excitation of the thus excited molecules, heat is generated leading to a local expansion of the gas causing a positive pressure pulse.

The excessive heat generated in this way subsequently escapes to a heat sink leading to a contraction of the gas causing a negative pressure pulse. A heat sink may be provided by a holder that is in physical contact to the photoacoustic gas analyzer 100.

Since the gas molecules of the type that is to be detected are excited in a time-varying fashion, e.g., periodically, a time-varying, e.g., periodic, pressure fluctuation is generated in the gas containing the type of molecules that are to be detected. Hence acoustic waves are generated in this way that may be detected by a sensor 110 positioned at a second axial end of the tubular housing 102.

Here, it is to be noted that the acoustic waves generated by the excitation of the molecules of the type that is to be detected and that are detectable by the sensor 110 are not necessarily induced in the gas received in the gas chamber 104, but may be instead generated in a reference gas chamber that will be described in detail in the following.

The photoacoustic gas analyzer 100 may be used for monitoring the composition of ambient air, e.g., for determining the content of $CO_2$ and/or of toxic gases such as of CO in ambient air. Methane and/or water molecules (humidity) in ambient air may also be detected in this way. Alternatively or additionally, the photoacoustic gas analyzer 100 may be configured and used as a breath analyzer to measure the content of alcohol and/or acetone which is indicative of the blood glucose level.

The excitation element 106 may include or may be configured as a radiation source 114 configured to emit radiation. The radiation emitted by the radiation source 114 may be suitable to selectively excite gas molecules of a specific type that are to be detected in the gas to be analyzed in a time-varying fashion, thereby generating acoustic waves in the way discussed above.

The radiation source 114 may be configured to emit electromagnetic radiation, e.g., in the infrared and/or in the visible and/or in the ultraviolet frequency range. Infrared light is suitable for exciting vibrational molecular modes. By way of example, infrared light with a wavelength of about 4.25 µm is suitable for exciting vibrational modes of a $CO_2$ molecule.

The radiation source 114 may include at least one of a group including: a black-body radiator, a photodiode, and a laser. Power supply lines 116 of a such configured radiation source 114 are shown in FIG. 1.

A black-body radiator is configured to emit electromagnetic radiation according to Planck's law, meaning that the spectrum emitted by it is determined by its temperature, not by its shape or composition. The radiation source 114 may include a black-body radiator configured as an electrically heatable body such as a membrane. The black-body radiator may be heated up to several hundreds of degrees Celsius, e.g., to about 600° C. in operation.

The sensor 110 may include or may be configured as a capacitive acoustic wave sensor having two membranes spaced apart from each other and defining a capacitor therebetween. One of the membranes may be be fixed and the respective other one may be displaceable by acoustic waves to be detected. A displacement of the displaceable membrane is indicative of characteristics of the acoustic waves to be detected and induces a change of the capacitance of the capacitor that can be detected by a suitable read-out circuit providing an electric signal indicative of characteristics of the acoustic waves to be detected such as of the acoustic pressure.

Additionally or alternatively, the sensor 110 may include or may be configured as a piezoelectric acoustic wave sensor having a piezoelectric thin film that is deformable by acoustic waves to be detected. A deformation of the piezoelectric thin film generates an electric voltage therein that is indicative of characteristics of the acoustic waves to be detected. The induced electric voltage may be read out by a suitable read-out circuit providing an electric signal indicative of characteristics of the acoustic waves to be detected such as of the acoustic pressure.

The photoacoustic gas analyzer 100 may include an excitation unit 118 that houses the excitation element 106 therein. The excitation unit 118 may be at least in part inserted into the first axial end 108 of the tubular housing 102.

The excitation unit 118 may include a plate-like excitation unit bottom portion 120 positioned outside of the tubular housing 102 and having an outer diameter $D_E$ larger than an inner diameter $D_1$ of the first axial end 108 of the tubular housing 102. As indicated in FIG. 1, the excitation unit bottom portion 120 may be in physical contact with an axial end surface 122 of the first axial end 108 of the tubular housing 102. In this way, the excitation unit bottom portion 120 may serve as a positioning means for accurately positioning the excitation element 106 with respect to the tubular housing 102.

As shown in FIG. 1, the radiation source 114 may be mounted on the excitation unit bottom portion 120 and the power supply lines 116 thereof may extend through the excitation unit bottom portion 120. The radiation source 114 may be mounted on the excitation unit bottom portion 120 such as to emit radiation in the axial direction A of the tubular housing 102.

The excitation unit 118 may further include an excitation unit insertion portion 124 extending from the excitation unit bottom portion 120 in the axial direction of the first axial end 108 of the tubular housing 102 and inserted into the first axial end 108 of the tubular housing 102.

The outer surface of the excitation unit insertion portion 124 may be in physical contact with an inner surface of the first axial end 108 of the tubular housing 102 and may be fixed thereto, e.g., by gluing.

In an exemplary embodiment, the outer diameter $d_E$ of the excitation unit insertion portion 124 may decrease with increasing distance from the excitation unit bottom portion 120. In this way, the insertion of the excitation unit insertion portion 124 into the first axial end 108 can be performed in a simple way. In this respect, it is also conceivable to provide the excitation unit insertion portion 124 at an axial end adjacent the excitation unit bottom portion 120 with an outer diameter $d_E$ which is equal to or slightly larger than the inner diameter $D_1$ of the first axial end 108 of the tubular housing 102. In this way, the excitation unit insertion portion 124 may be brought into frictional engagement with the inner surface of the first axial end 108 of the tubular housing 102 for fixing the excitation unit 118 thereto.

As shown in FIG. 1, the photoacoustic gas analyzer 100 may further include an excitation unit window 126 positioned at an axial end of the excitation unit insertion portion 124 opposite to the excitation unit bottom portion 120.

The excitation unit window 126 may be configured to transmit the radiation emitted by the radiation source 114. The excitation unit window 126 may be configured as a filter. By means of the filter 126, the radiation spectrum of the radiation source 114 may be limited to a narrow energy band to make sure that only molecules of a single type are excited at a given time, i.e., that molecules of other types than those that are to be detected are not unintentionally also excited which may deteriorate the measurement accuracy.

In case only a single type of gas molecules is to be detected in the gas to be analyzed, the filter 126 may be configured to have fixed transmission characteristics. Alternatively, in case gas molecules of different types having different excitation energies are to be detected in the gas to be analyzed, a tunable filter 126 with tunable transmission characteristics may be employed. In operation, the transmission characteristics of the filter 126 can be varied to excite molecules of different types. The filter 126 may include or may be configured as a plasmonic filter and/or a Fabry-Perot interferometer.

The excitation unit bottom portion 120, the excitation unit insertion portion 124, and the excitation unit window 126 may define a substantially gas-tight volume 127 that houses the excitation element 106 and that is filled with an inert gas such as nitrogen or a noble gas. The oxidation of an excitation element 106 configured as a black-body radiator can be efficiently avoided by means of the inert gas.

As shown in FIG. 1, the photoacoustic gas analyzer 100 may include a sensor unit 128 that houses the sensor 110 therein. The sensor unit 128 may be at least in part inserted into the second axial end 112 of the tubular housing 102.

The sensor unit 128 may include a plate-like sensor unit bottom portion 130 positioned outside of the tubular housing 102 and having an outer diameter $D_S$ larger than an inner diameter $D_2$ of the second axial end 112 of the tubular housing 102. As indicated in FIG. 1, the sensor unit bottom portion 130 may be in physical contact with an axial end surface 132 of the second axial end 112 of the tubular housing 102. In this way, the sensor unit bottom portion 130 may serve as a positioning means for accurately positioning the sensor 110 with respect to the tubular housing 102.

The sensor unit 128 may further include a sensor unit insertion portion 134 extending from the sensor unit bottom portion 130 in the axial direction of the second axial end 112 of the tubular housing 102 and inserted into the second axial end 112 of the tubular housing 102.

The outer surface of the sensor unit insertion portion 134 may be in physical contact with an inner surface of the second axial end 112 of the tubular housing 102 and may be fixed thereto, e.g., by gluing.

In an exemplary embodiment, the outer diameter $D_S$ of the sensor unit insertion portion 134 may decrease with increasing distance from the sensor unit bottom portion 130. In this way, the insertion of the sensor unit insertion portion 134 into the second axial end 112 of the tubular housing 102 can be performed in a simple way. It is also conceivable to provide the sensor unit insertion portion 134 at an axially outermost end adjacent the sensor unit bottom portion 130 with a diameter $d_S$ which is equal to or slightly larger than the inner diameter $D_2$ of the second axial end 112 of the tubular housing 102. In this way, the sensor unit insertion portion 134 may be brought into frictional engagement with the inner surface of the second axial end 112 of the tubular housing 102 for fixing the sensor unit 128 thereto.

The gas chamber 104 may be defined between the excitation unit 118 and the sensor unit 128. As shown in FIG. 1, the housing wall 103 of the tubular housing 102 may include several through holes 136a, 136b serving as inlets/outlets for the gas to be analyzed. In this way, the gas chamber 104 may be in permanent fluid flow communication with its environment. Consequently, a permanent monitoring of the composition of the gas surrounding the photoacoustic gas analyzer 100 may be realized in this way.

In an exemplary embodiment (not shown in FIG. 1), a direct detection scheme may be employed, i.e. the sensor 110 may be positioned in the gas chamber 104 to detect acoustic waves generated by excited gas molecules in the gas chamber 104 by means of the excitation element 106. In such a direct detection scheme, the response of the sensor 110 would increase with increasing content of molecules of a given type that are selectively excited by the excitation element 106.

Alternatively, as shown in FIG. 1, the sensor 110 may be positioned outside of the gas chamber 104 in a substantially gas-tight reference gas chamber 138 defined by the sensor unit bottom portion 130, the sensor unit insertion portion 134 and a sensor unit window 140. The reference gas chamber 138 may be filled with a reference gas containing one or several types of gas that are to be detected in the gas to be analyzed in the gas chamber 104. The sensor unit window 140 may be transparent for radiation emitted by the radiation source 114 in order to excite molecules of the reference gas in the reference gas chamber 138.

By means of this setup a differential detection scheme is realized. If no gas molecules of the type to be detected are present in the gas chamber 104, the radiation emitted by the radiation source 114 excites gas molecules only in the reference gas chamber 138. As described above, acoustic waves are generated as a result of this excitation which are detectable by the sensor 110. The sensor response is maximum if no gas molecules of the type to be detected are present in the gas chamber 104. With increasing content of gas molecules of the type to be detected in the gas received in the gas chamber 104, the sensor response decreases as compared to the maximum sensor response, since a part of the radiation emitted by the radiation source 114 is absorbed in the gas chamber 104 so that the radiation power in the reference gas chamber 138 is reduced. This reduction of the sensor response is indicative of the content of gas molecules of the type of interest in the gas chamber 104.

The sensor unit window 140 may include or may be configured as a filter configured to selectively transmit the excitation radiation emitted by the radiation source 114. In case only a single type of gas molecules is to be detected in the gas to be analyzed, the filter may be configured to have fixed transmission characteristics. Alternatively, in case gas molecules of different types having different excitation energies are to be detected in the gas to be analyzed, a tunable filter with tunable transmission characteristics may be employed. In operation, the transmission characteristics of the filter can be varied to excite molecules of different types. The filter may include or may be configured as a plasmonic filter and/or a Fabry-Perot interferometer.

Starting from the setup shown in FIG. 1, a direct detection scheme may be provided by omitting the sensor unit window 140. In this way, the interior of the sensor unit 128 would form a part of the gas chamber 104 so that acoustic waves generated by the selective excitation of the gas molecules would be directly detectable by the sensor 110, meaning that the sensor response increases with increasing concentration of the gas molecules of interest in the gas to be analyzed.

The sensor 110 may be mounted on the sensor unit bottom portion 130 and may include power and/or signal lines 142 passing through the sensor unit bottom portion 130. In addition, a read-out circuit 144 coupled to the sensor 110 may be also mounted on the sensor unit bottom portion 130, e.g., on the surface thereof facing to the interior of the sensor unit 128. The read-out circuit 144 may be configured to analyze signals output by the sensor 110 and to determine the content of gas molecules of a given type in the gas to be analyzed. The read-out circuit 144 may include an application-specific integrated circuit (ASIC).

As shown in FIG. 1, the radiation source 114 and the sensor 110 may be positioned in a face-to-face relationship relative to each other. In this way, radiation emitted by the radiation source 114 is emitted towards the sensor 110. Hence, a setup is provided in this way that enables a highly efficient excitation of gas molecules in the gas chamber 104 or in the reference gas chamber 138.

The excitation efficiency can be increased by providing a reflector 146 on the housing wall 103 of the tubular housing 102. As indicated in FIG. 1, the housing wall 103 of the tubular housing 102 may have a layered structure with a radially inner layer 148 transparent for the excitation radiation, and a radially outer layer configured as the reflector 146. The radially inner insulating layer 148 may be made of a thermally insulating material. The thermal conductivity of the material of the thermally insulating material may be less than 20 W/(m·K), less than 10 W/(m·K) or even less than 5 W/(m·K).

As shown in FIG. 1, only the radially inner layer 148 may be in physical contact with the excitation unit 118 and/or the sensor unit 128. Hence, the excitation element 106 and the sensor 110 can be thermally decoupled from each other in this way, in case the radially inner layer 148 is made of a thermally insulating material.

The reflector 146 may be configured as a thin metallic film. The reflector 146 may have a reflectance in the infrared and/or in the visible and/or in the ultraviolet frequency range of at least 20% or of at least 50% or even of at least 80%.

By means of the reflector 146 provided on the housing wall 103 of the tubular housing 102, the tubular housing 102 acts like an optical fibre enabling a highly efficient excitation of molecules of the type to be detected. In addition, the reflector 146 may inhibit external radiation such as ambient light from entering the gas chamber 104. In this way, an unintentional excitation of molecules in the gas chamber 104 can be avoided.

Even though the housing wall 103 of the tubular housing 102 is shown in FIG. 1 with a substantially circular cylindrical shape, its shape is not limited thereto. Other shapes, e.g., with a rectangular or polygonal cross-sectional configuration, are also conceivable. In addition, housing walls 103 with a non-rectilinear axial extension are also conceivable.

The excitation unit 118 and/or the sensor unit 128 may be provided as pre-assembled units. In this way, the manufacturing of the photoacoustic gas analyzer 100 can be performed in a simple way, simply by inserting the excitation unit 118 and/or the sensor unit 128 into respective axial ends of the tubular housing 102 and fixing them thereto, e.g. by frictional engagement.

The excitation unit 118 and/or the sensor unit 128 may be configured as transistor outline (TO) cans.

In an exemplary embodiment the photoacoustic gas analyzer 100 may have a length of about 20 mm and a diameter of about 5 mm. These exemplary outer dimensions of the photoacoustic gas analyzer 100 show that it may be easily mounted into a mobile device such as a mobile phone. It should be noted that the gas analyzer 100 may be alternatively configured as a non-dispersive detector such as a non-dispersive infrared detector (NDIR). As such, it may also have the above-described structure of the photoacoustic gas analyzer 100 except that the sensor 110 would not be configured as an acoustic wave sensor, but as a radiation detector configured to detect radiation emitted by the radiation source 114 and transmitted through the gas to be analyzed. Similar to the photoacoustic gas analyzer 100 described above, the radiation emitted by the radiation source 114 may be configured to selectively excite molecules of a specific type in the gas to be analyzed. The absorbance level of the gas to be analyzed is correlated with the content of the molecules of the given type in the gas to be analyzed. More specifically, the higher the concentration of the molecules of the given type in the gas to be analyzed is, the higher will be the absorbance level and the lower will be the response of the sensor 110. Consequently, the response of the radiation sensor of a such configured gas analyzer is indicative of the content of the molecules of the given type.

In the following, various aspects of the present disclosure will be described.

Example 1 is a gas analyzer. The gas analyzer may include: a tubular housing having a housing wall extending along an axial direction of the tubular housing and surrounding a gas chamber configured to receive a gas to be analyzed therein, an excitation element positioned at a first axial end of the tubular housing and configured to selectively excite gas molecules of a specific type that is to be detected in the gas received in the gas chamber in a time-varying fashion, thereby generating acoustic waves, and a sensor positioned at a second axial end of the tubular housing and configured to detect acoustic waves generated by the excitation element.

In Example 2, the subject matter of Example 1 can optionally further include that the excitation element includes or is configured as a radiation source configured to emit radiation. The radiation may be adapted to selectively excite in a time-varying fashion the type of gas molecules that are to be detected.

In Example 3, the subject matter of Example 2 can optionally further include that the radiation source is configured to emit electromagnetic radiation.

In Example 4, the subject matter of Example 3 can optionally further include that the radiation source is configured to emit electromagnetic radiation in the infrared and/or in the visible and/or in the ultraviolet frequency range.

In Example 5, the subject matter of Example 4 can optionally further include that the radiation source includes at least one of a group including: a black-body radiator, a photodiode, and a laser.

In Example 6, the subject matter of Example 5 can optionally further include that the radiation source includes a black-body radiator configured as an electrically heatable body such as a membrane.

In Example 7, the subject matter of any one of Examples 2 to 6 can optionally further include a filter configured to selectively transmit radiation of a predetermined energy emitted by the radiation source.

In Example 8, the subject matter of Example 7 can optionally further include that the filter is configured as a tunable filter with tunable transmission characteristics.

In Example 9, the subject matter of any one of Examples 7 or 8 can optionally further include that the filter includes or is configured as a plasmonic filter and/or a Fabry-Perot interferometer.

In Example 10, the subject matter of any one of Examples 1 to 9 can optionally further include an excitation unit that houses the excitation element therein. The excitation unit may be at least in part inserted into the first axial end of the tubular housing.

In Example 11, the subject matter of Example 10 can optionally further include that the excitation unit includes: a plate-like excitation unit bottom portion positioned outside of the tubular housing and having an outer diameter larger than an inner diameter of the first axial end of the tubular housing, and an excitation unit insertion portion extending from the excitation unit bottom portion in the axial direction of the first axial end. The excitation unit insertion portion may be inserted into the first axial end of the tubular housing.

In Example 12, the subject matter of Example 11 can optionally further include that the outer diameter of the excitation unit insertion portion decreases with increasing distance from the excitation unit bottom portion.

In Example 13, the subject matter of any one of Examples 11 or 12 can optionally further include an excitation unit window positioned at an axial end of the excitation unit insertion portion opposite to the excitation unit bottom portion.

In Example 14, the subject matter of Example 13 and of any one of Examples 2 to 9 can optionally further include that the excitation unit window is configured to transmit the radiation emitted by the radiation source.

In Example 15, the subject matter of Example 14 and of any one of Examples 7 to 9 can optionally further include that the excitation unit window is configured as a filter.

In Example 16, the subject matter of any one of Examples 13 to 15 can optionally further include that the excitation unit bottom portion, the excitation unit insertion portion, and the excitation unit window define a substantially gas-tight volume that houses the excitation element and that is filled with an inert gas such as nitrogen or a noble gas.

In Example 17, the subject matter of any one of Examples 11 to 16 can optionally further include that the excitation element is mounted on the excitation unit bottom portion.

In Example 18, the subject matter of any one of Examples 1 to 17 can optionally further include a sensor unit that houses the sensor therein. The sensor unit may be at least in part inserted into the second axial end of the tubular housing.

In Example 19, the subject matter of Example 18 can optionally further include that the sensor unit includes: a plate-like sensor unit bottom portion positioned outside of the tubular housing and having an outer diameter larger than an inner diameter of the second axial end of the tubular housing, and a sensor unit insertion portion extending from the sensor unit bottom portion in the axial direction of the second axial end. The sensor unit insertion portion may be inserted into the second axial end of the tubular housing.

In Example 20, the subject matter of Example 19 can optionally further include that the outer diameter of the sensor unit insertion portion decreases with increasing distance from the sensor unit bottom portion.

In Example 21, the subject matter of any one of Examples 19 or 20 can optionally further include a sensor unit window positioned at an axial end of the sensor unit insertion portion opposite to the sensor unit bottom portion.

In Example 22, the subject matter of Example 21 and of any one of Examples 2 to 9 can optionally further include that the sensor unit window is configured to transmit the radiation emitted by the radiation source.

In Example 23, the subject matter of Example 22 and of any one of Examples 7 to 9 can optionally further include that the sensor unit window is configured as a filter.

In Example 24, the subject matter of any one of Examples 21 to 23 can optionally further include that the sensor unit bottom portion, the sensor unit insertion portion, and the sensor unit window define a substantially gas-tight volume housing the sensor and filled with a gas of the type to be detected.

In Example 25, the subject matter of any one of Examples 18 to 23 can optionally further include that the interior of the sensor unit defines at least a part of the gas chamber.

In Example 26, the subject matter of Example 25 can optionally further include that the interior of the sensor unit is in permanent gas flow communication with the exterior of the gas analyzer.

In Example 27, the subject matter of any one of Examples 19 to 26 can optionally further include that the sensor is mounted on the sensor unit bottom portion.

In Example 28, the subject matter of any one of Examples 10 to 17 and of any one of Examples 18 to 27 can optionally further include that at least a part of the gas chamber is located between the excitation unit and the sensor unit in the axial direction of the tubular housing and is delimited in the radial direction of the tubular housing by the housing wall.

In Example 29, the subject matter of Example 28 can optionally further include that the part of the housing wall of the tubular housing delimiting the gas chamber includes at least one through hole formed therethrough and providing a gas passage between the gas chamber and the exterior of the gas analyzer.

In Example 30, the subject matter of any one of Examples 2 to 29 can optionally further include that at least a part of or even the entire housing wall of the tubular housing surrounding the gas chamber is equipped with a reflector configured to reflect the radiation emitted by the radiation source.

In Example 31, the subject matter of Example 30 can optionally further include that the reflector has a reflectance in the infrared and/or in the visible and/or in the ultraviolet frequency range of at least 20% or of at least 50% or even of at least 80%.

In Example 32, the subject matter of any one of Examples 30 or 31 can optionally further include that the housing wall of the tubular housing has a layered structure including a radially inner layer that is transparent for the radiation emitted by the radiation source and a radially outer layer configured as the reflector.

In Example 33, the subject matter of Example 32 can optionally further include that the radially inner layer is made of a thermally insulating material.

Example 34 is a gas analyzer. The gas analyzer may include a tubular housing having a housing wall extending along an axial direction of the tubular housing and surrounding a gas chamber configured to receive a gas to be analyzed therein, a radiation source positioned at a first axial end of the tubular housing and configured to emit electromagnetic radiation that is configured to selectively excite gas molecules of a specific type that is to be detected in the gas received in the gas chamber, and a sensor positioned at a second axial end of the tubular housing and configured to detect electromagnetic radiation emitted by the radiation source.

In Example 35, the subject matter of Example 34 can optionally further include that the radiation source is configured to emit electromagnetic radiation in the infrared and/or in the visible and/or in the ultraviolet frequency range.

In Example 36, the subject matter of Example 35 can optionally further include that the radiation source includes at least one of a group including: a black-body radiator, a photodiode, and a laser.

In Example 37, the subject matter of Example 36 can optionally further include that the radiation source includes a black-body radiator configured as an electrically heatable body such as a membrane.

In Example 38, the subject matter of any one of Examples 34 to 37 can optionally further include a filter configured to selectively transmit radiation of a predetermined energy emitted by the radiation source.

In Example 39, the subject matter of Example 38 can optionally further include that the filter is configured as a tunable filter with tunable transmission characteristics.

In Example 40, the subject matter of any one of Examples 38 or 39 can optionally further include that the filter includes or is configured as a plasmonic filter and/or a Fabry-Perot interferometer.

In Example 41, the subject matter of any one of Examples 34 to 40 can optionally further include an excitation unit that houses the radiation source therein. The excitation unit may be at least in part inserted into the first axial end of the tubular housing.

In Example 42, the subject matter of Example 41 can optionally further include that the excitation unit includes: a plate-like excitation unit bottom portion positioned outside of the tubular housing and having an outer diameter larger than an inner diameter of the first axial end of the tubular housing, and an excitation unit insertion portion extending from the excitation unit bottom portion in the axial direction of the first axial end. The excitation unit insertion portion may be inserted into the first axial end of the tubular housing.

In Example 43, the subject matter of Example 42 can optionally further include that the outer diameter of the excitation unit insertion portion decreases with increasing distance from the excitation unit bottom portion.

In Example 44, the subject matter of any one of Examples 42 or 43 can optionally further include an excitation unit window positioned at an axial end of the excitation unit insertion portion opposite to the excitation unit bottom portion.

In Example 45, the subject matter of Example 44 can optionally further include that the excitation unit window is configured to transmit the radiation emitted by the radiation source.

In Example 46, the subject matter of Example 45 and of any one of Examples 38 to 40 can optionally further include that the excitation unit window is configured as a filter.

In Example 47, the subject matter of any one of Examples 44 to 46 can optionally further include that the excitation unit bottom portion, the excitation unit insertion portion, and the excitation unit window define a substantially gas-tight volume that houses the radiation source and that is filled with an inert gas such as nitrogen or a noble gas.

In Example 48, the subject matter of any one of Examples 42 to 47 can optionally further include that the radiation source is mounted on the excitation unit bottom portion.

In Example 49, the subject matter of any one of Examples 34 to 48 can optionally further include a sensor unit that houses the sensor therein. The sensor unit may be at least in part inserted into the second axial end of the tubular housing.

In Example 50, the subject matter of Example 49 can optionally further include that the sensor unit includes: a plate-like sensor unit bottom portion positioned outside of the tubular housing and having an outer diameter larger than an inner diameter of the second axial end of the tubular housing, and a sensor unit insertion portion extending from the sensor unit bottom portion in the axial direction of the second axial end. The sensor unit insertion portion may be inserted into the second axial end of the tubular housing.

In Example 51, the subject matter of Example 50 can optionally further include that the outer diameter of the sensor unit insertion portion decreases with increasing distance from the sensor unit bottom portion.

In Example 52, the subject matter of any one of Examples 50 or 51 can optionally further include a sensor unit window positioned at an axial end of the sensor unit insertion portion opposite to the sensor unit bottom portion.

In Example 53, the subject matter of Example 52 can optionally further include that the sensor unit window is configured to transmit the radiation emitted by the radiation source.

In Example 54, the subject matter of Example 53 and of any one of Examples 38 to 40 can optionally further include that the sensor unit window is configured as a filter.

In Example 55, the subject matter of any one of Examples 49 to 54 can optionally further include that the interior of the sensor unit defines at least a part of the gas chamber.

In Example 56, the subject matter of Example 55 can optionally further include that the interior of the sensor unit is in permanent gas flow communication with the exterior of the gas analyzer.

In Example 57, the subject matter of any one of Examples 50 to 56 can optionally further include that the sensor is mounted on the sensor unit bottom portion.

In Example 58, the subject matter of any one of Examples 41 to 48 and of any one of Examples 49 to 57 can optionally further include that at least a part of the gas chamber is located between the excitation unit and the sensor unit in the axial direction of the tubular housing and is delimited in the radial direction of the tubular housing by the housing wall.

In Example 59, the subject matter of Example 58 can optionally further include that the part of the housing wall of the tubular housing delimiting the gas chamber includes at least one through hole formed therethrough and providing a gas passage between the gas chamber and the exterior of the gas analyzer.

In Example 60, the subject matter of any one of Examples 34 to 59 can optionally further include that the sensor is configured as or includes a photodiode and/or a thermocouple.

In Example 61, the subject matter of any one of Examples 34 to 60 can optionally further include that at least a part of or even the entire housing wall of the tubular housing surrounding the gas chamber is equipped with a reflector configured to reflect the radiation emitted by the radiation source.

In Example 62, the subject matter of Example 61 can optionally further include that the reflector has a reflectance in the infrared and/or in the visible and/or in the ultraviolet frequency range of at least 20% or of at least 50% or even of at least 80%.

Example 63 is a mobile device including a gas analyzer of any one of Examples 1 to 62.

In Example 64, the mobile device of Example 63 can be configured as a mobile phone.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A gas analyzer, comprising:
   a tubular housing having a housing wall extending along an axial direction of the tubular housing and surrounding a gas chamber configured to receive a gas to be analyzed therein;
   an excitation element positioned at a first axial end of the tubular housing and configured to selectively excite gas molecules of a specific type in a time-varying fashion to generate acoustic waves; and
   a sensor positioned at a second axial end of the tubular housing and configured to detect acoustic waves generated by the excitation element;
   a sensor unit that houses the sensor therein, wherein the sensor unit is at least in part inserted into the second axial end of the tubular housing, the sensor unit comprising:
   a plate-like sensor unit bottom portion positioned outside of the tubular housing and having an outer diameter larger than an inner diameter of the second axial end of the tubular housing, and
   a sensor unit insertion portion extending from the sensor unit bottom portion in the axial direction from the second axial end towards the first axial end, wherein the sensor unit insertion portion is inserted into the second axial end of the tubular housing,
   a sensor unit window positioned at an axial end of the sensor unit insertion portion opposite to the sensor unit bottom portion, so that the sensor unit insertion portion extends within the tubular housing from the sensor unit bottom portion to the sensor unit window;
   wherein the sensor unit bottom portion, the sensor unit insertion portion, and the sensor unit window enclose a substantially gas-tight reference gas chamber that is partially occupied by the sensor and that is filled with a gas of the type to be detected.

2. The gas analyzer of claim 1,
   wherein the excitation element comprises or is configured as a radiation source configured to emit radiation, wherein the radiation is adapted to selectively excite in a time-varying fashion the type of gas molecules that is to be detected.

3. The gas analyzer of claim 2,
   wherein the radiation source is configured to emit electromagnetic radiation.

4. The gas analyzer of claim 3,
   wherein the radiation source is configured to emit electromagnetic radiation in the infrared and/or in the visible and/or in the ultraviolet frequency range.

5. The gas analyzer of claim 4,
   wherein the radiation source comprises at least one of a group comprising: a black-body radiator, a photodiode, and a laser.

6. The gas analyzer of claim 5,
   wherein the radiation source comprises the black-body radiator configured as an electrically heatable body.

7. The gas analyzer of claim 2,
further comprising a filter configured to selectively transmit radiation of a predetermined energy emitted by the radiation source.

8. The gas analyzer of claim 7,
wherein the filter is configured as a tunable filter with tunable transmission characteristics.

9. The gas analyzer of claim 2,
wherein at least a part of or even the entire housing wall of the tubular housing surrounding the gas chamber is equipped with a reflector configured to reflect the radiation emitted by the radiation source.

10. The gas analyzer of claim 9,
wherein the housing wall of the tubular housing has a layered structure including a radially inner layer that is transparent for the radiation emitted by the radiation source and a radially outer layer configured as the reflector.

11. The gas analyzer of claim 10,
wherein the radially inner layer is made of a thermally insulating material.

12. The gas analyzer of claim 1,
comprising an excitation unit that houses the excitation element therein, wherein the excitation unit is at least in part inserted into the first axial end of the tubular housing.

13. The gas analyzer of claim 12,
wherein the excitation unit comprises:
a plate-like excitation unit bottom portion positioned outside of the tubular housing and having an outer diameter larger than an inner diameter of the first axial end of the tubular housing, and
an excitation unit insertion portion extending from the excitation unit bottom portion in the axial direction of the first axial end, wherein the excitation unit insertion portion is inserted into the first axial end of the tubular housing.

14. The gas analyzer of claim 13,
further comprising an excitation unit window positioned at an axial end of the excitation unit insertion portion opposite to the excitation unit bottom portion.

15. The gas analyzer of claim 14,
wherein the excitation unit window is configured as a filter configured to selectively transmit radiation of a predetermined energy emitted by the radiation source.

16. The gas analyzer of claim 14,
wherein the excitation unit bottom portion, the excitation unit insertion portion, and the excitation unit window define a substantially gas-tight volume that houses the excitation element and that is filled with an inert gas.

17. The gas analyzer of claim 16, wherein the inert gas comprises nitrogen and/or a noble gas.

18. The gas analyzer of claim 1,
wherein the sensor unit window is configured as a filter configured to selectively transmit radiation of a predetermined energy emitted by the radiation source.

19. The gas analyzer of claim 1,
comprising an excitation unit that houses the excitation element therein, wherein the excitation unit is at least in part inserted into the first axial end of the tubular housing,
wherein at least a part of the gas chamber which is configured to receive the gas to be analyzed is located between the excitation unit and the sensor unit in the axial direction of the tubular housing and is delimited in the radial direction of the tubular housing by the housing wall.

20. The gas analyzer of claim 19,
wherein the part of the housing wall of the tubular housing delimiting the gas chamber comprises at least one through hole formed therethrough and providing a gas passage between the gas chamber and the exterior of the gas analyzer.

21. The gas analyzer of claim 1, wherein an outer surface of the sensor unit insertion portion is in physical contact with an inner surface of the tubular housing.

22. A gas analyzer, comprising:
a tubular housing having a housing wall extending along an axial direction of the tubular housing and surrounding a gas chamber configured to receive a gas to be analyzed therein;
an excitation element positioned at a first axial end of the tubular housing and configured to selectively excite gas molecules of a specific type in a time-varying fashion to generate acoustic waves; and
a sensor positioned at a second axial end of the tubular housing in a reference gas chamber and configured to detect acoustic waves generated by the excitation element;
an excitation unit that houses the excitation element therein, wherein the excitation unit is at least in part inserted into the first axial end of the tubular housing, wherein the excitation unit comprises:
a plate-like excitation unit bottom portion positioned outside of the tubular housing and having an outer diameter larger than an inner diameter of the first axial end of the tubular housing, and
an excitation unit insertion portion extending from the excitation unit bottom portion in the axial direction from the first axial end towards the second axial end, wherein the excitation unit insertion portion is inserted into the first axial end of the tubular housing,
an excitation unit window positioned at an axial end of the excitation unit insertion portion opposite to the excitation unit bottom portion so that the excitation unit insertion portion extends within the tubular housing from the excitation unit bottom portion to the excitation unit window;
wherein the excitation unit bottom portion, the excitation unit insertion portion, and the excitation unit window enclose a substantially gas-tight volume which is partially occupied by the excitation element and that is filled with an inert gas, and
wherein an outer surface of the excitation unit insertion portion is in physical contact with an inner surface of the tubular housing.

23. The gas analyzer of claim 22, wherein the defined gas-tight volume is located between the excitation unit window and the excitation element, and wherein the excitation unit window is located distal to the excitation unit along the axial direction.

* * * * *